United States Patent [19]
Trulaske et al.

[11] Patent Number: 5,618,245
[45] Date of Patent: Apr. 8, 1997

[54] FITNESS APPARATUS WITH HEART RATE CONTROL SYSTEM AND METHOD OF OPERATION

[75] Inventors: Frank R. Trulaske, St. Louis, Mo.; Phillip M. Singer, Clarendon Hills, Ill.

[73] Assignee: True Fitness Technology, Inc., St. Louis, Mo.

[21] Appl. No.: 585,191

[22] Filed: Jan. 11, 1996

Related U.S. Application Data

[63] Continuation-in-part of Ser. No. 549,604, Oct. 27, 1995, abandoned, which is a continuation of Ser. No. 192,407, Feb. 4, 1994, Pat. No. 5,462,504.

[51] Int. Cl.⁶ .................................................. A63B 21/005
[52] U.S. Cl. ...................... 482/7; 482/6; 482/8; 482/54; 482/900; 128/707
[58] Field of Search ............................... 482/1–9, 54, 57, 482/64, 900–902; 601/23, 24, 26, 33–35; 128/695 R, 696, 700, 707

[56] References Cited

U.S. PATENT DOCUMENTS

| | | |
|---|---|---|
| Re. 33,088 | 10/1989 | Jones et al. . |
| 3,518,985 | 7/1970 | Quinton . |
| 3,759,248 | 9/1973 | Valiquette . |
| 4,051,841 | 10/1977 | Thoma . |
| 4,441,705 | 4/1984 | Brown . |
| 4,513,295 | 4/1985 | Jones et al. . |
| 4,535,774 | 8/1985 | Olson . |
| 4,686,987 | 8/1987 | Salo et al. . |
| 4,708,337 | 11/1987 | Shyu . |
| 4,788,983 | 12/1988 | Brink et al. . |
| 4,884,575 | 12/1989 | Sanders . |
| 4,970,528 | 11/1990 | Beaufort et al. . |
| 4,976,424 | 12/1990 | Sargeant et al. . |
| 4,998,725 | 3/1991 | Watterson et al. . |
| 5,001,632 | 3/1991 | Hall-Tipping . |
| 5,067,710 | 11/1991 | Watterson et al. ................... 482/64 |
| 5,083,772 | 1/1992 | Brown . |
| 5,190,035 | 3/1993 | Salo et al. . |
| 5,207,621 | 5/1993 | Koch et al. . |
| 5,368,532 | 11/1994 | Farent ................................... 482/5 |
| 5,527,239 | 6/1996 | Abbondanza ......................... 482/3 |

OTHER PUBLICATIONS

"Your Body & Spirit" Promotional brochure.
"The Next Step Forward" brochure.

*Primary Examiner*—Richard J. Apley
*Assistant Examiner*—Glenn E. Richman

[57] ABSTRACT

A method and apparatus for maintaining the heart rate of a user of a fitness apparatus at a scheduled target rate by varying the resistance of a first resistance mechanism with respect to a second resistance mechanism. To increase the heart rate, the resistance of the first resistance mechanism is increased to a maximum level before an adjustment is made to the second resistance mechanism. To decrease the heart rate, the resistance of the second resistance mechanism is decreased to a minimum level before an adjustment is made to the first resistance mechanism. The invention may be incorporated into a treadmill having resistance mechanisms including a mechanism to vary the speed of the treadmill belt and a mechanism to vary the grade of the treadmill.

11 Claims, 13 Drawing Sheets

FITNESS APPARATUS WITH HEART RATE CONTROL SYSTEM AND METHOD OF OPERATION

CROSS-REFERENCE TO RELATED APPLICATIONS

This application is a continuation-in-part of U.S. patent application Ser. No. 08/549,604, abandoned, Apr. 23, 1996, filed Oct. 27, 1995, which is a continuation of U.S. patent application Ser. No. 08/192,407, filed Feb. 4, 1994, now U.S. Pat. No. 5,462,504.

FIELD OF THE INVENTION

The invention relates generally to exercise equipment, and in particular to a method and apparatus for dynamically varying resistance mechanisms of a fitness apparatus in dependence on the user's heart rate.

BACKGROUND OF THE INVENTION

Modern fitness apparatuses, or exercise machines, including treadmills, steppers, stationary bicycles, and the like are often electronically controlled to vary their resistance levels. For example, stationary bicycles are electronically controlled to vary their resistance over the duration of an exercise routine to simulate uphill, level and downhill riding conditions. This varies the routine, purportedly to prevent the user of the apparatus from becoming bored with the otherwise repetitive exercise.

At the same time, it is also known to measure the heart rate or pulse of the user and adjust the level of exercise accordingly to maximize the cardiovascular benefits achieved from physical exercise without wasting time and effort. This also provides the benefit of being able to quickly detect dangerously high or accelerating heart rates.

To this end, pulse detection circuitry has been coupled with exercise equipment which provides a display to the user and/or a supervisor corresponding to the actual heart rate being achieved. The user or the supervisor can then make adjustments to the resistance level to adjust the heart rate as needed.

In U.S. Pat. No. 4,998,725, a microprocessor varies the incline of a treadmill or the resistance to the pedalling of a stationary bicycle to achieve a target heart rate. Adjustment of the resistance is only generally disclosed as increasing the resistance to increase the heart rate and decreasing the resistance to decrease the heart rate.

Several types of exercise equipment have more than a single variable resistance mechanism that affects the user's heart rate. For example, conventional treadmills have both variable inclines and variable speeds, while many stationary bicycles have variable pedal resistance for the lower body as well as resistance-based exercise mechanisms for the upper body. Since numerous such mechanisms are often intended to be operated simultaneously, the resulting heart rate depends on the resistance of all operating mechanisms and their relationship to each other and to the heart rate. At the same time, the conditioning of the skeletal muscle groups being exercised depend on which resistance mechanisms are being varied. Although exercise equipment comprising interrelated resistance mechanisms have become increasingly popular, the prior art varies only a single one of the mechanisms to control heart rate. The results are unsatisfactory because achieving a target heart rate in such equipment by merely increasing or decreasing one of the resistance mechanisms does not consider and compensate for the benefits or detriments that may occur by varying the resistance of the other such mechanisms in relation thereto.

SUMMARY OF THE INVENTION

Accordingly, it is a primary object of the invention to provide an apparatus and method for dynamically controlling the resistance of a first resistance mechanism with respect to the resistance of at least one other resistance mechanism of a fitness apparatus in dependence on the heart rate of the user thereof.

It is a related object to provide a fitness apparatus of the above kind that optimizes the benefit obtained from exercise thereon.

It is another object to provide an apparatus and method as characterized above that is capable of benefitting virtually any user regardless of their level of physical conditioning.

It is yet another object to provide a fitness apparatus of the above kind that may further incorporate conventional features and alternative modes of operation.

It is a resulting feature that the fitness apparatus may be combined with electronic heart rate supervision to ensure the safety of the user.

Briefly, the invention provides a fitness apparatus for controlling the heart rate of a user with respect to a predetermined target heart rate, and includes pulse detection circuitry for regularly sensing the heartbeat of the user and providing a signal corresponding thereto. A first and second resistance mechanism are provided, both having resistance levels that vary in response to electrical signals. In addition, there is provided a controller including a processor, input circuitry operatively connected to receive external signals from the pulse detection circuitry and communicate the signals to the processor, and output circuitry operatively connected to the first resistance mechanism and the second resistance mechanism for independently transmitting electrical signals from the processor thereto. As the processor receives the pulse signal from the pulse detection circuitry, it determines the heart rate of the user, and, employing comparison circuitry therein, compares the heart rate of the user with the target heart rate. If the heart rate of the user is lower than the target heart rate, the processor provides electrical output signals to increase the resistance level of only the first resistance mechanism until a predetermined upper resistance limit is reached, before providing electrical output signals to increase the resistance level of the second exercise mechanism. If the heart rate of the user is higher than the target heart rate, the processor provides electrical output signals to decrease the resistance level of only the second resistance mechanism until a predetermined lower resistance limit is reached, before providing electrical output signals to decrease the resistance level of the first exercise mechanism.

The user may input data including the target heart rate and/or the maximum resistance levels, the data may be recalled from memory, or the maximum resistance levels may be determined by the processor based upon the resistance levels when the actual heart rate of the user achieves the target heart rate. The invention may be incorporated into a treadmill having resistance mechanisms including a mechanism to vary the speed of the treadmill belt and a mechanism to vary the grade of the treadmill. In the treadmill embodiment, the processor may determine the maximum speed and grade based upon the current speed and grade when the measured heart rate of the user achieves the target heart rate.

Other objects and advantages will become apparent from the following detailed description when taken in conjunction with the drawings, in which:

Figure 1:
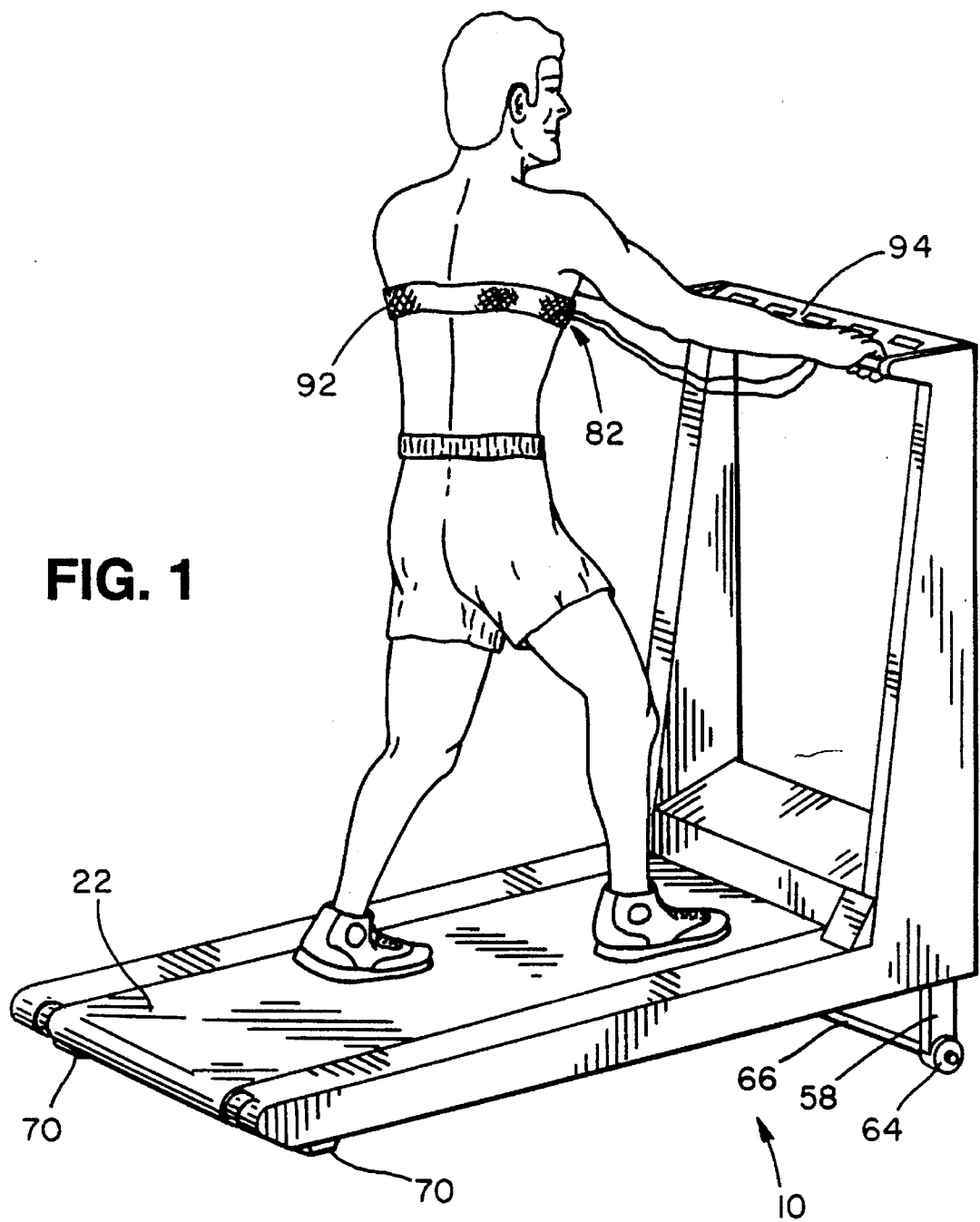
FIG. 1 is a perspective view illustrating a treadmill and user thereon having heart rate monitoring capabilities according to one aspect of the invention.

While the invention is susceptible of various modifications and alternative constructions, a certain illustrated embodiment thereof is shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention.

DETAILED DESCRIPTION OF THE PREFERRED EMBODIMENT

Figure 2:
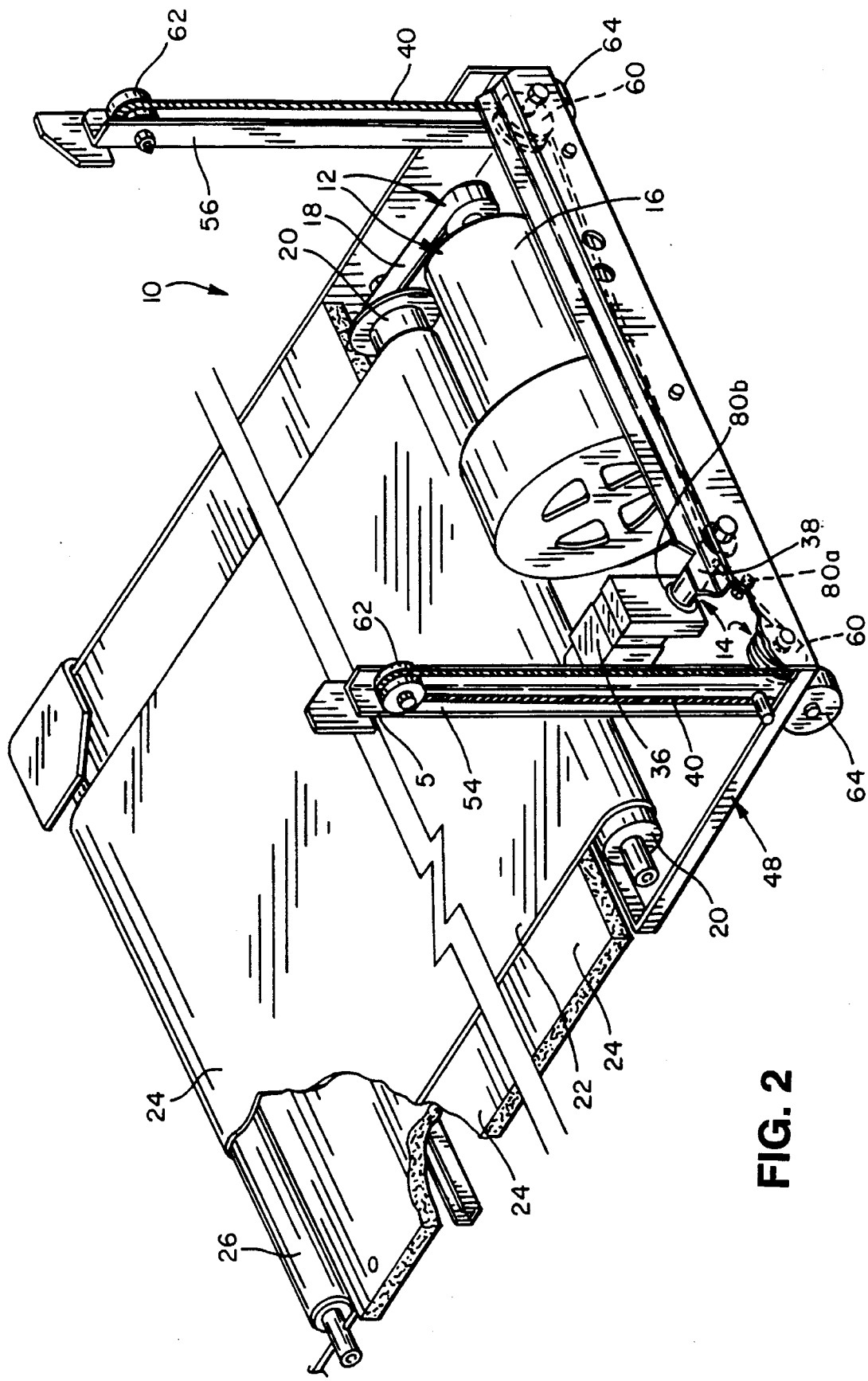
FIG. 2 is a left front partial view of the treadmill of FIG. 1 illustrating the resistance mechanisms when at a level grade.
Figure 3:
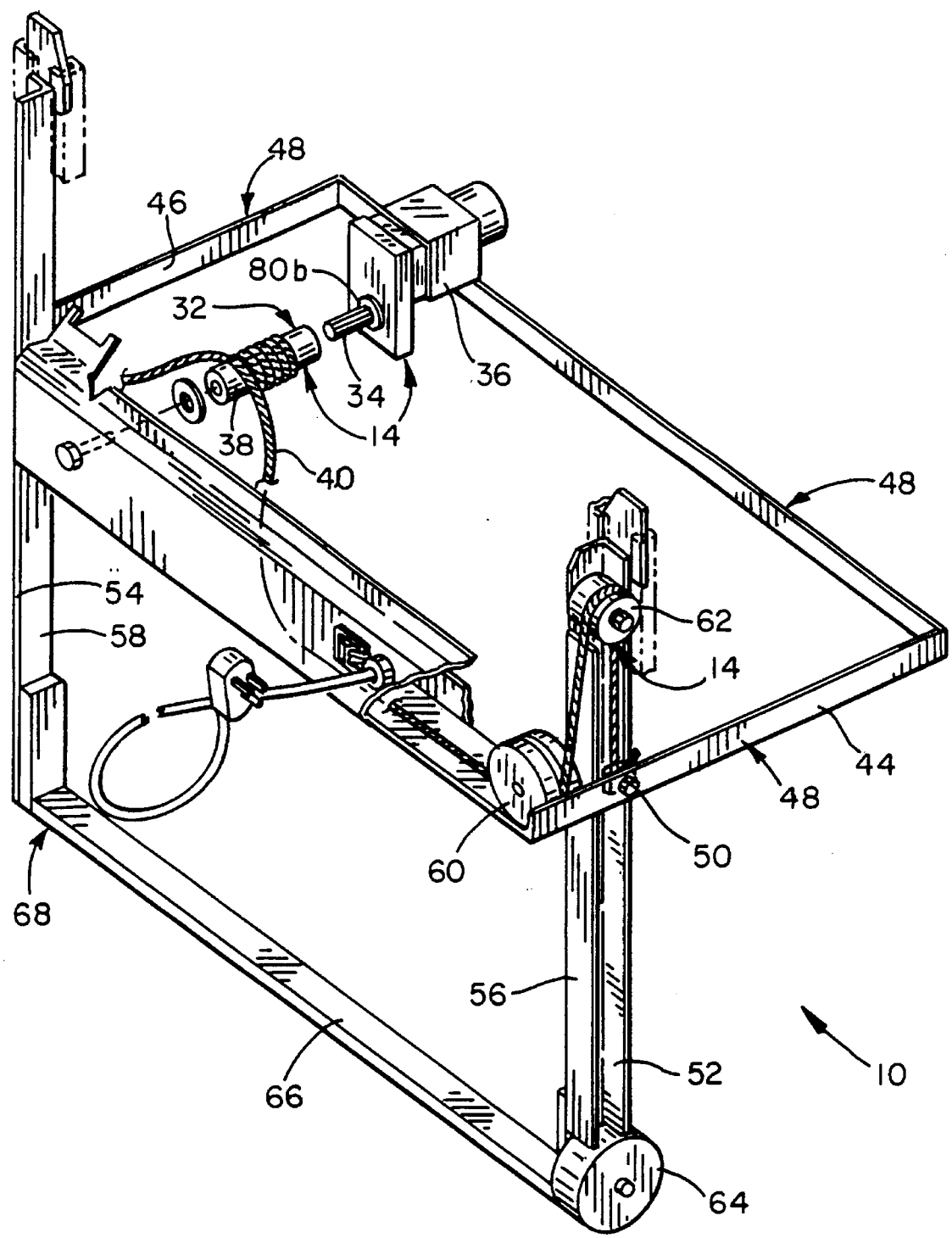
FIG. 3 is a right front partial view of the treadmill illustrating the resistance mechanism for varying the grade of the treadmill shown at an inclined grade.

Turning now to the drawings and referring first to FIGS. 1–3, there is shown a fitness apparatus in the form of a treadmill generally designated 10 having a plurality of resistance mechanisms incorporated therein. In the treadmill 10 described herein, the first resistance mechanism 12 (best seen in FIG. 2) consists of a speed-varying mechanism while the second resistance mechanism takes the form of a grade-adjustment mechanism 14 (best seen in FIG. 3).

FIGS. 2 and 3 are left front and right front partial views of a treadmill having speed and grade incline mechanisms that can be controlled in accordance with one aspect of the invention as described in more detail below. One such treadmill, the HRC 700 (and other Heart Rate Control treadmills in the HRC series including the HRC 300) is available from True Fitness Technologies, Inc., O'Fallon, Mo.

To vary the speed of the treadmill 10, and thus increase the resistance of the first resistance mechanism 12, a variable-speed drive motor 16 is mechanically coupled in a conventional manner by a drive belt 18 to a drive roller 20 to rearwardly move a rotating surface, i.e., a continuous belt 22 riding upon a low-friction support surface 24. Although it is preferable to employ the drive belt 18 to couple the drive roller 20 to the drive motor 16, it can be appreciated that gears or the like may be alternatively employed. A freely-rotating rear roller 26 is provided to redirect the continuous belt 22 forwardly beneath the support surface 24 in the conventional manner.

The continuous belt 22 is arranged so as to not slip on the drive roller 20 under ordinary loads, for example by providing proper tensioning, coefficients of friction and/or having treads in the underside of the belt 22 underside to mate with the drive roller 20. Thus, as the drive motor 16 rotates at any given speed, the belt 22 rotates with a speed corresponding thereto.

Figure 4A:
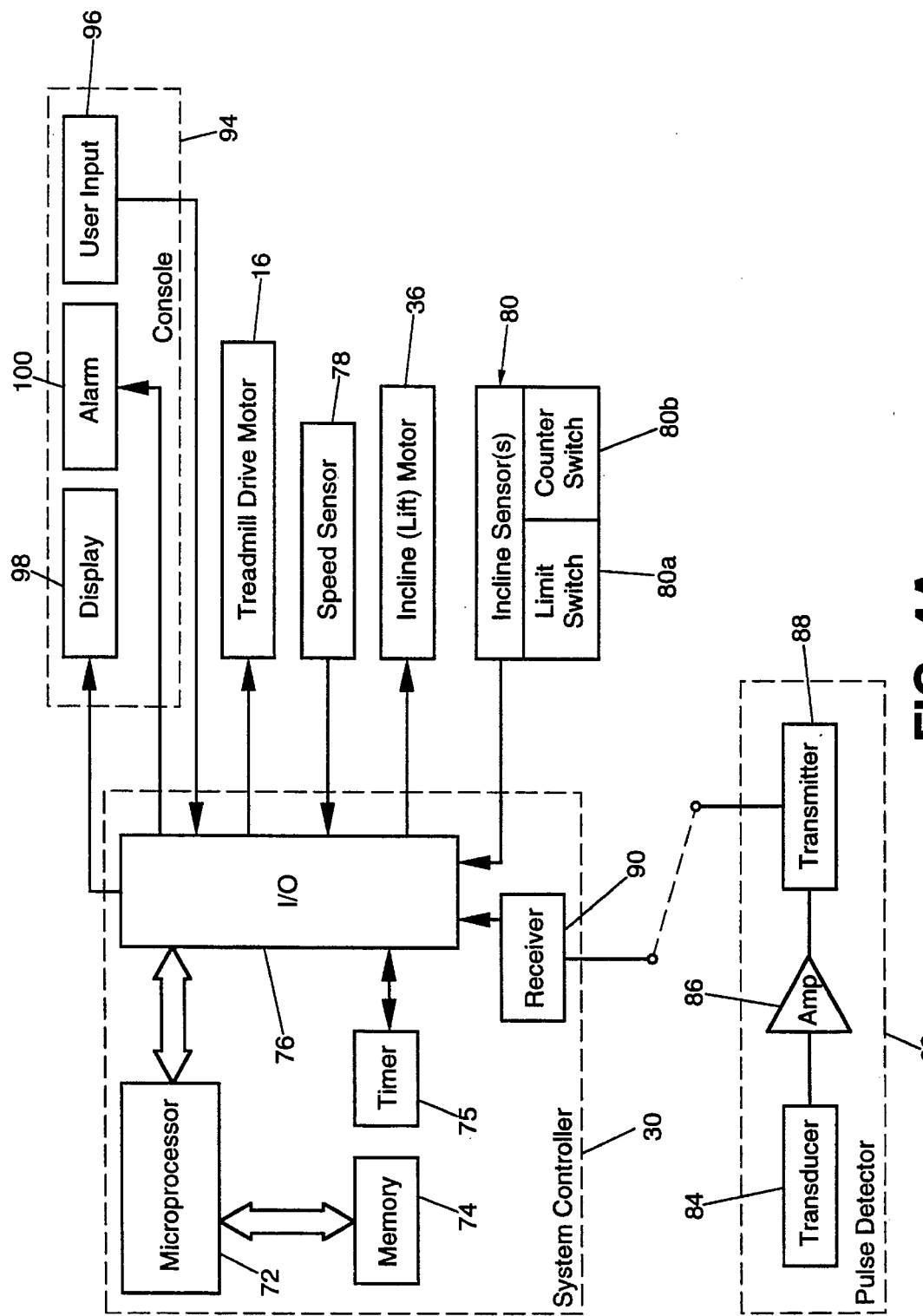
FIG. 4A is a block diagram of the electronic control system for controlling a fitness apparatus including its resistance mechanisms in accordance with the invention.
Figure 4B:
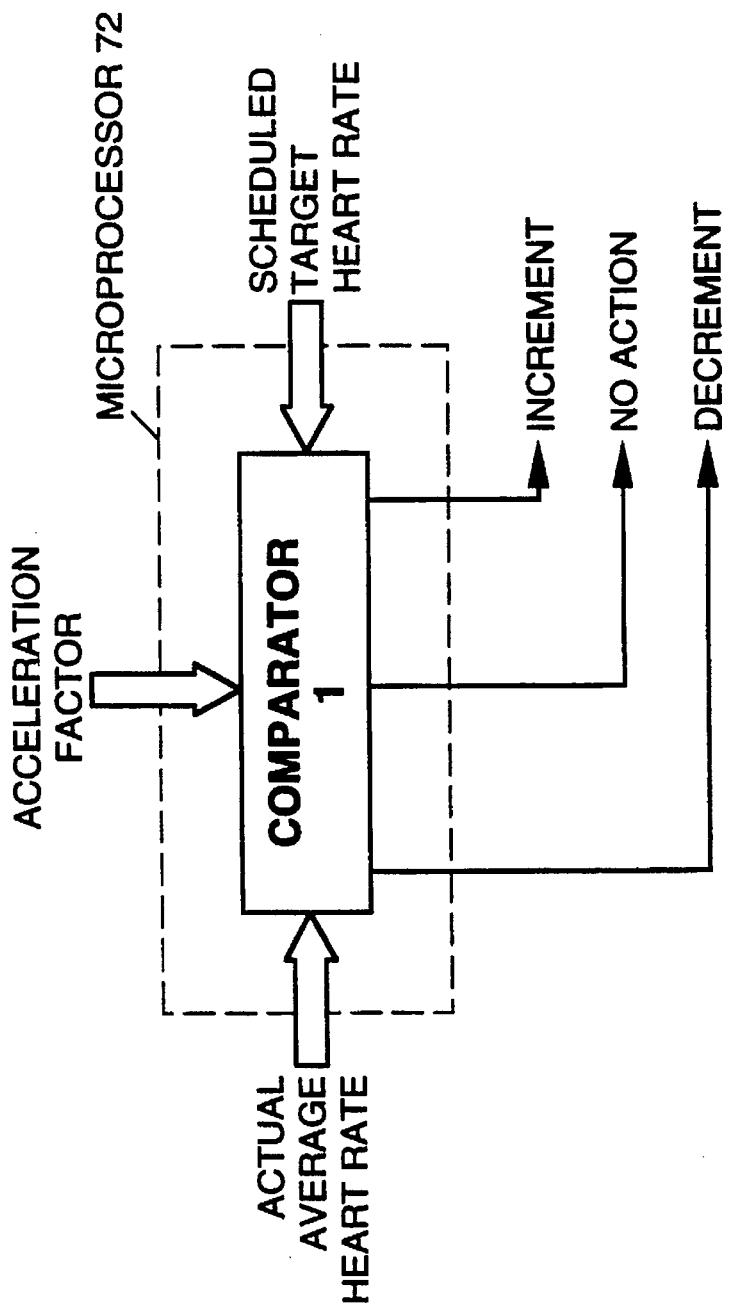
FIGS. 4B–4D are state machine diagrams representing functions performed by the processing circuitry of FIG. 4A in accordance with received and stored data.
Figure 4C:
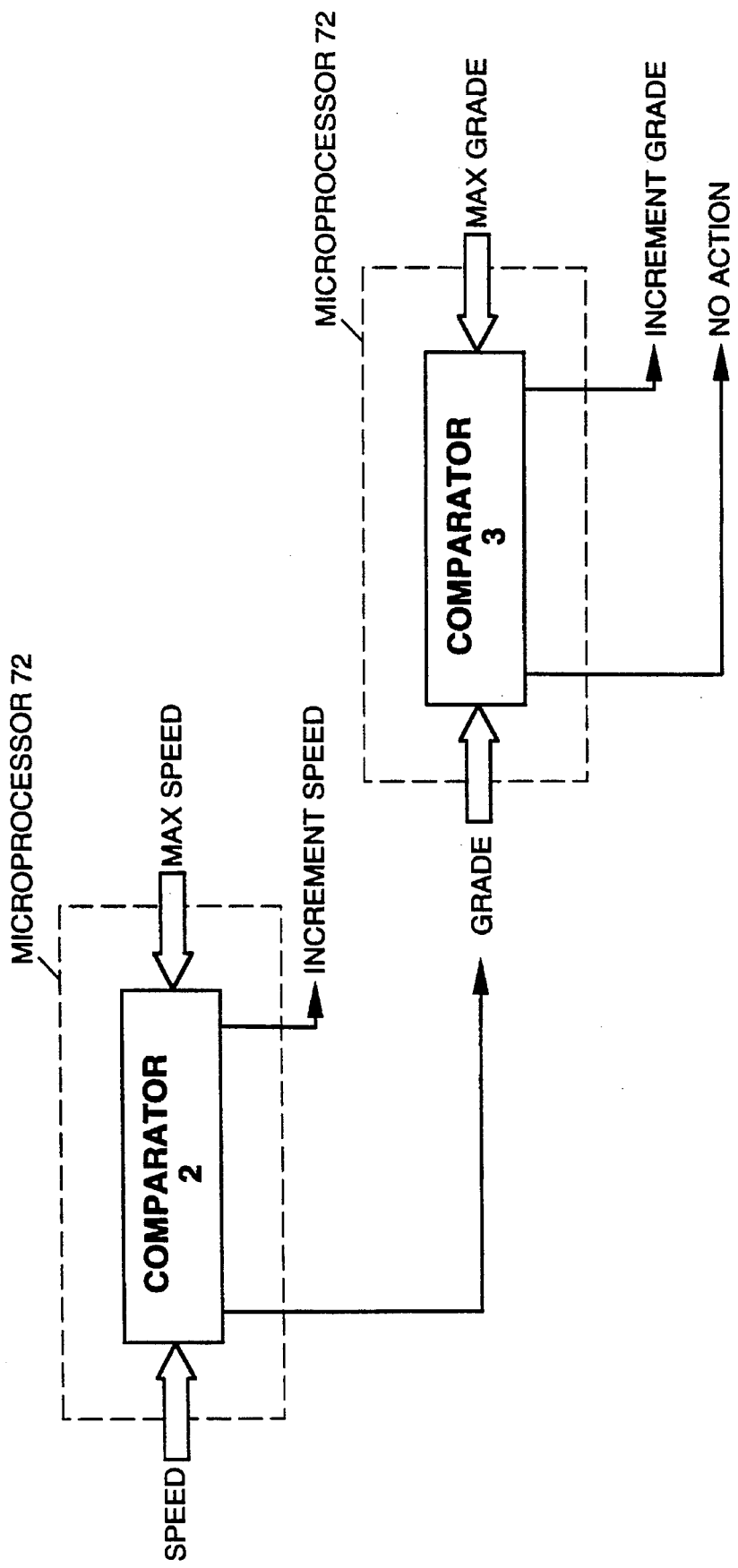

Regardless of how configured, the drive motor 16 is operated by drive signals from a system controller 30, illustrated in FIG. 4A, and may, for example, be a stepping motor, in which event the signals are pulses. Preferably, the drive motor is a DC motor, such as one commercially available from Pacific Scientific, Rockford, Ill., Model No. 3644-4811-7, for which the drive signals are voltages of appropriate levels applied to the motor for specified periods of time. In any case, the system controller 30, described in more detail below, provides one or more signals that ultimately determine the resistance level of the first resistance mechanism 12, i.e., the speed of the treadmill 10 in the illustrated embodiment. In a preferred embodiment, the controller 30 adjusts the speed between 0.0 miles per hour and 10.0 miles per hour in one-tenth of a mile per hour increments.

To vary the grade (i.e.; the incline angle) of the rotating treadmill surface, and thus increase the resistance of the second resistance mechanism 14 by altering the amount of exertion required by the user to remain on the apparatus 10, a conventional motor-driven windlass 32 is employed (FIG. 3). To this end, an incline motor 36, such as one commercially available from Rex Engineering, Miami, Fla., Model No. APS 12T 8FB, is mechanically coupled at its shaft 34 to a drum or cylinder 38 having a cable 40 threaded therethrough so that rotating the drum winds or unwinds the cable 40 to raise or lower a lift frame 48 as the incline motor 36 is operated.

As best shown in FIGS. 2 and 3, the ends of the cable 40 are connected by bolts 50 or the like to the left and right members 44, 46 of the lift frame 48 as considered from the perspective of an ordinary user upon the apparatus. The lift frame 48 rides up and down in guide channels 52, 54 incorporated in left and right front legs 56, 58, respectively. At each of the sides, the cable 40 rides on a pulley system wherein a first pulley wheel 60 is connected to the lift frame 48, and a second pulley wheel 62 is connected to the upper end of its corresponding leg (56 left, 58 right). Wheels 64 at the lower portion of each of the legs 56, 58 are preferably added to enhance the portability of the apparatus 10.

A stabilizing crossbar 66 connects the lower portions of the left and right legs 56, 58 forming a U-shaped support base 68. Since the rear portion of the device rests on supports 70, by operating the incline motor 36 to wind the cable 40 around the windlass drum 38, the cable 40 pulls the lift frame 48 upwardly relative to the support base 68 thus elevating the front end of the treadmill 10. Operating the incline motor 36 in the reverse direction lowers the front end.

The incline motor 36 is operated by signals from the controller 30 and may, for example, be a stepping motor, in which event the signals are pulses, or an AC or DC motor, in which event the signals cause voltages of appropriate levels to be applied to the incline motor 36 for specified periods of time. For example, in a preferred embodiment a conventional treadmill incline mechanism is employed wherein the signal activates a relay which applies power to a fractional AC motor until the grade is incremented by the desired amount. In any case, the controller 30 provides one or more signals that ultimately determine the resistance level of the second resistance mechanism 14, i.e., the grade of the treadmill in the exemplified embodiment. In a preferred embodiment, the controller 30 adjusts the grade between 0.0 percent (level, or 0.0 degrees) and 16 percent in one-half percent increments. Note that the incline motor 36 is preferably a reversible motor of a type that remains locked in position when power is removed so that the cable does not unwind due to gravitational force. Alternatively, mechanical means such as gears, stops and the like may provide the reversibility and locking features.

Preferably, as shown in more detail in FIG. 4A, the system controller 30 includes a microprocessor 72, a memory 74, a timer 75 and input/output (I/O) circuitry 76 connected in a conventional manner. A preferred microprocessor is an 80C31 available from Intel Corporation, although it can be appreciated that any suitable microprocessor may be utilized. The memory 74 is intended to include random access memory (RAM), read-only memory (ROM), or any other type of storage means. The I/O circuitry 76 ordinarily includes conventional buffers, drivers, relays and the like, such as for driving the motors 16, 36 with sufficient power. Conventional circuitry for latching output signals from the microprocessor 72 is ordinarily included in the output circuitry 76 where appropriate. Thus, output signals from the microprocessor 72, interfaced through appropriate output circuitry 76, control the treadmill drive motor 16 and incline motor 36.

Although the speed and grade of the apparatus is determined by (and thereby ordinarily known to) the controller 30, it is preferable to include a speed sensor 78 for detecting the actual speed of the unit and an incline sensor 80 for determining the grade. Such sensors are well known, and for example the speed sensor 72 is preferably a Hall-effect type disposed to provide a value to the controller 30 indicative of the revolutions per minute of the drive roller 20. The controller 30 subsequently converts this value to miles per hour.

Ordinarily, the incline sensor 80 comprises an appropriately positioned limit switch 80a that determines 0.0 percent grade and a counter switch 80b that indicates an amount of incline motor 36 rotation, and may further include an upper limit switch which is actuated at a maximum incline. For example, as is common in treadmills, to increase or decrease the incline of the lift frame 48, in a closed-loop motor control operation the controller 30 ordinarily provides an output signal which causes a relay within output circuitry 76 to apply power of the appropriate polarity to the incline motor 36. The incline motor 36 then rotates in the appropriate direction until the counter switch 80b in the incline sensor 80 indicates an amount of rotation corresponding to a one-half percent of grade increase or decrease, at which time the signal (and power) is removed.

Figure 5A:
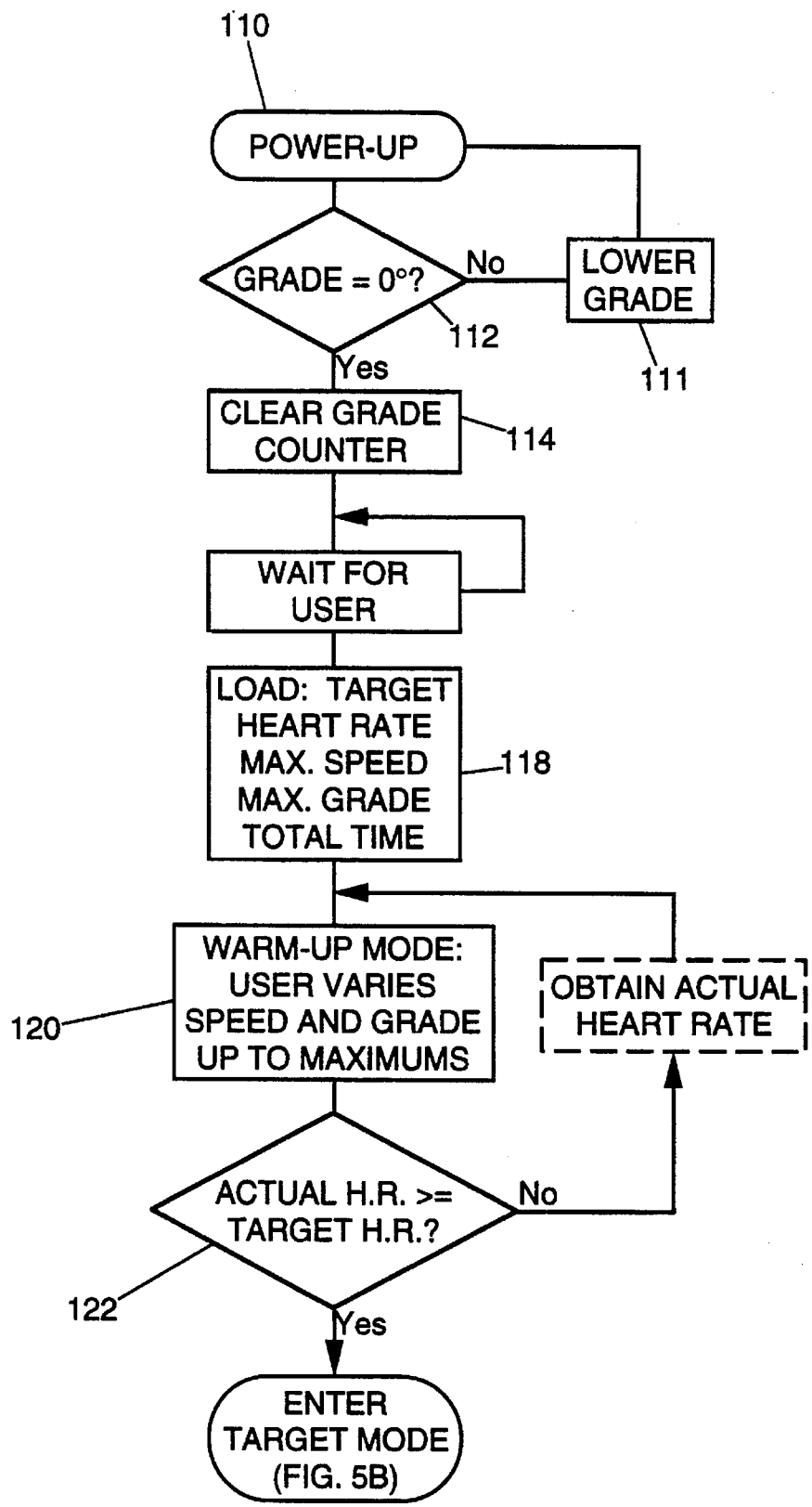
FIGS. 5A–5C comprise a flow diagram of the general controller software steps for implementing the invention in a treadmill.

As shown in step 110 of FIG. 5A, upon power-up of the apparatus 10, the controller 30 initially operates the incline motor 36 to lower the lift frame 48 (step 111) to 0.0 percent grade as indicated by the incline sensor 80 (step 112), i.e., upon actuation of the appropriately positioned limit switch 80a. This actuation takes place, for example, as a portion of the cable 40 contacts the switch 80a, a condition which only occurs when the cable 40 is fully unwound. Once lowered, an internal byte reserved in memory 74, acting as a counter to record the number of increments and decrements to the incline motor 36, is zeroed at step 114. This internal counter is incremented and decremented whenever the grade is increased or decreased by an incremental step, as indicated by counter switch 80b, for example during the adjustment procedure as described in more detail below. Thus, at all times the controller 30 is aware of the amount of incline of the treadmill 10, and will not provide signals to adjust the incline beyond the corresponding upper limit (16 percent, or a count of +32 increments) or the lower limit (0 percent, or a count of 0 increments).

If desired, an upper limit switch may be further added, so that the controller 30 does not solely rely on an incremented or decremented counter in its memory 74 to determine the upper incline limit, which can be significant if an error or memory failure occurs. For example, the cable 40 might become overly tightened during an attempt to increase the grade if the controller memory 74 contained a recorded value indicating that the cable 40 is unwound, due to a loss of memory contents or other error, when in fact the cable 40 is already fully wound. The addition of an upper limit sensor provides an additional safeguard to prevent this problem. If further desired, a clutch or other mechanical safety mechanism may be further provided in one or both of the motors 16, 36 to prevent damage thereto in the event of a sensor failure.

In accordance with one aspect of the invention, the resistance levels of the resistance mechanisms 12, 14 are varied with respect to one another in dependence on the actual (average) heart rate of the user. Accordingly, to detect the user's actual (average) heart rate, the apparatus employs pulse detection circuitry 82 (FIG. 4A) and a suitable timer, such as timer 75. Any conventional pulse detection circuitry will suffice, provided it is capable of supplying a signal corresponding to the user's heartbeat to the input circuitry 76 of the controller. As utilized herein, pulse detection circuitry includes electrocardiograph-type detection devices which sense electric currents or potentials on the user to provide a signal corresponding to the heartbeat, or any other type of devices which sense heartbeats and provide corresponding signals.

However, it is preferable to employ pulse detection circuitry comprising an electronic sensor such as transducer 84, (which may be electrodes), amplifier 86 and transmitter 88 to remotely communicate an appropriate signal, such as a signal at infrared or RF frequencies, to a suitable receiver 90 at the system controller 30 without the need for transmitting conductors.

For example, one such telemetry-type ECG transmitter system is attached to the user by chest belt 92 or the like so that the transducer 84 acting as the sensor contacts the user's skin just below the pectoral muscles. The transducer 84 picks up the user's heartbeat, and provides a signal which is then amplified and/or otherwise modified (such as by filtering and/or encoding) by amplifier 86 before being transmitted by transmitter 88 to the receiver 90 at the controller 30. To detect the heartbeat, the transducer 84 may comprise a pair of electrodes or the like which provide varying potential differences representative of the heartbeat to amplifier 86.

Although not necessary to the invention, it can be appreciated that in a commercial setting such as at a health club, it may be first necessary to encode the transmitted pulses so that each machine receives only pulses from a single, corresponding transmitter. To this end, digital or other well-known encoding and decoding techniques may be employed, and the receivers may further be programmable so as to function with any appropriate transmitter, but only one, at any time. In a preferred embodiment, the transmitter employs an RF frequency and includes microprocessor-based circuitry that combines an encryption code with the detected pulse for transmission to the receiver, so that the system responds only when receiving the proper code.

Regardless of how the pulse is detected, transmitted and received, an actual (average) heart rate is then determined at the controller 30, ordinarily by summing the amount of time between a known number of heartbeats and converting the total time to a number of beats per minute (bpm). Of course, the conversion of the detected pulse to the average heart rate may occur prior to transmission to the receiver such that a value indicative of the calculated heart rate may be transmitted to the controller 30 instead of individual pulses.

In any case, one such method of determining an actual (average) heart rate at the controller 30 consists of executing an interrupt routine upon the detection of a pulse, for example on its falling edge. In this manner, the heart rate is always being updated as it occurs, regardless of the current step being executed by the microprocessor 72. In the interrupt routine, a time is recorded for each pulse, and thus the measured heart rate for that pulse is calculated in bpm based on the time between the falling edges of that pulse and of the previous pulse. Preferably, a comparison with extreme limits, for example, comparing the heart rate to see if it is less than 30 bpm or greater than 250 bpm, is first performed to help eliminate bad pulses which may be caused by noise or the like. Consecutive bad readings may lead to an error condition.

Assuming the calculated heart rate is reasonable, in a preferred embodiment 4 consecutive (reasonable) readings are averaged together to determine the heart rate, defined herein as the actual or current (average) heart rate, to be compared against the scheduled target heart rate. Error corrections may be first made to the readings if significant changes in the times between individual pulses are detected, for example if the time difference corresponds to a heart rate that is outside of the previous average heart rate plus or minus 10 bpm.

Of course, when compared with the target heart rate to determine an adjustment direction as described in more detail below, the current actual average heart rate cannot be changed via the interrupt in the middle of a comparison or other calculation, and thus the value obtained in the interrupt is protected before being used in the calculations or comparisons. For example, this can be accomplished by setting a variable equal to the calculated average at a known point in the routine, and then using that variable in the comparison.

Figure 5B:
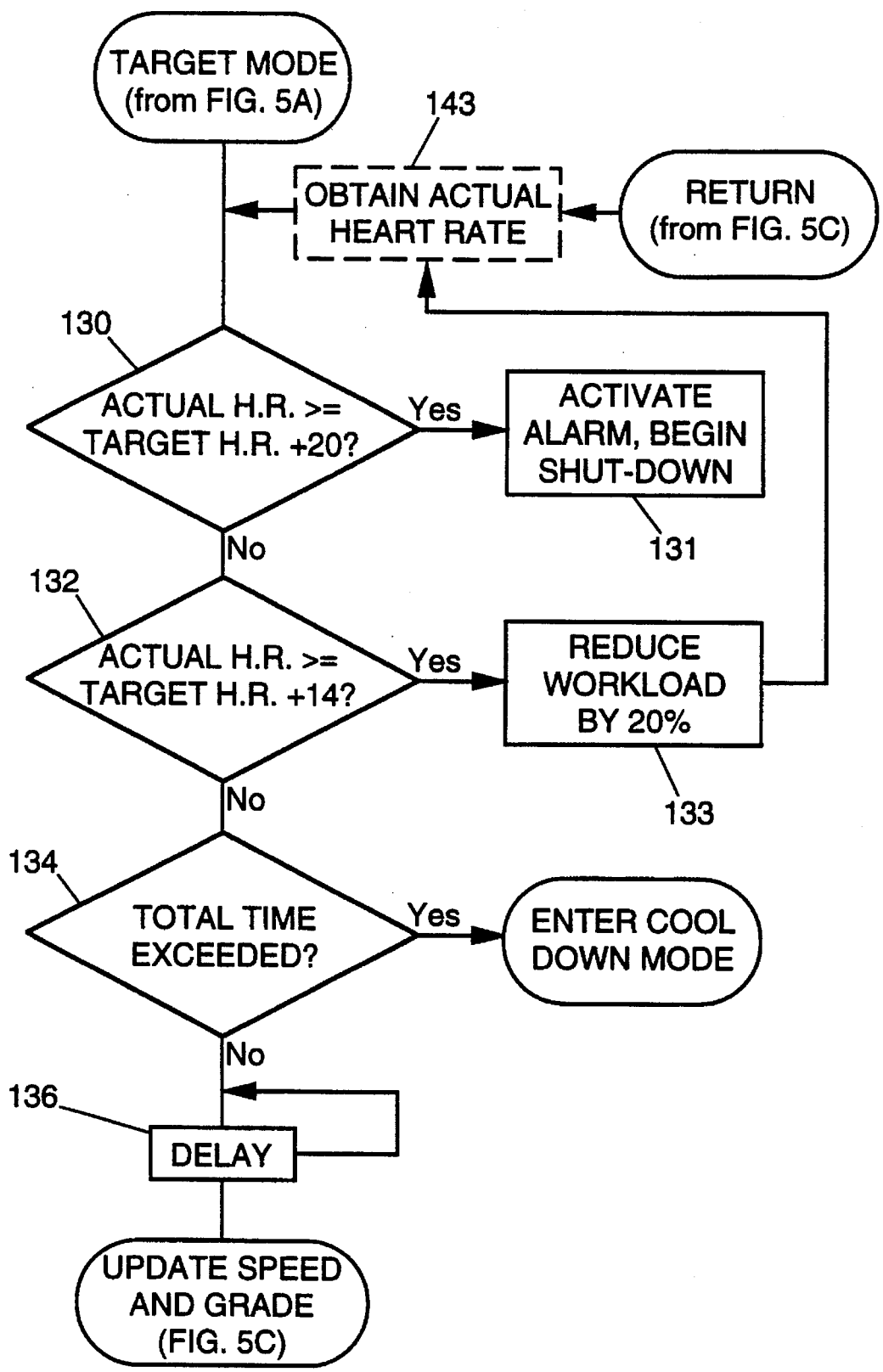
Figure 5C:
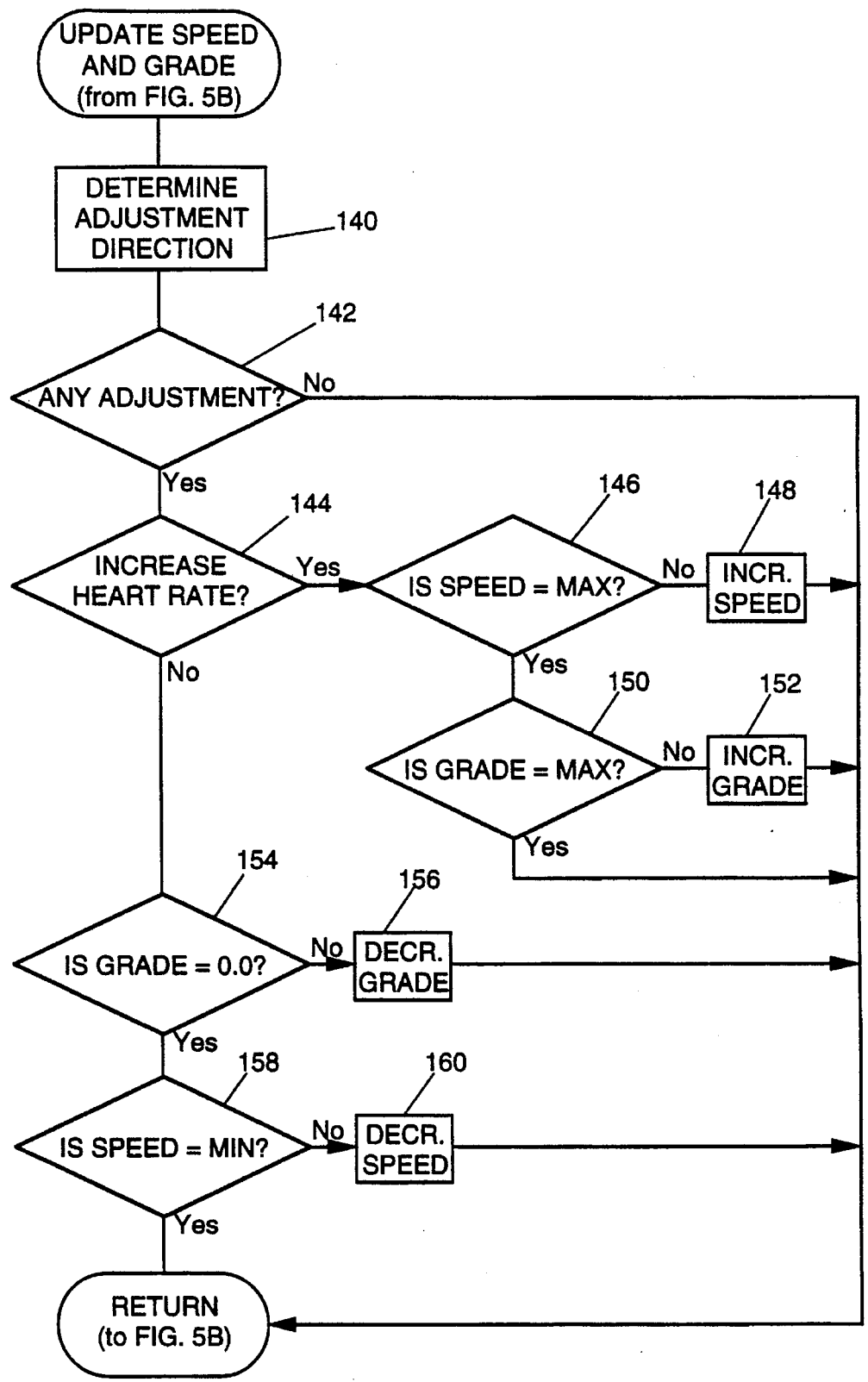

Regardless of how the heart rate is obtained and determined, once known to the controller 30, the controller 30 operates the resistance mechanisms 12, 14 in accordance with the invention as represented in the steps illustrated in the flowchart of FIGS. 5A–5C. Of course, it can be readily appreciated that the apparatus is capable of operating in any number of other desirable ways prior to or after executing the steps of FIGS. 5A–C.

Indeed, although not necessary to the invention, it is ordinarily preferable to have the user operate the fitness apparatus for a period of time prior to controlling the resistance mechanisms to achieve the desired (target) heart rate. Thus, a warm-up exercise period, in which the user first attains the desired heart rate level is first executed at step 120 as described in more detail below. Similarly, although again not necessary to the invention, it is often desirable to operate the apparatus at reduced resistance levels for a cool-down period in which the actual (average) heart rate gradually abates to lower levels, also described in more detail below.

In any event, at step 116 the apparatus waits for the user to initially enter or cause to be entered at step 118 a target heart rate, maximum grade, maximum speed, and a time duration for maintaining the actual (average) heart rate at the target level. Additionally, if desired, other variables such as a maximum heart rate for that particular user may be entered at that time. While the target heart rate may be a single fixed number (or range of heart rates above and/or below the input number), it is to be understood that any number of target heart rates may be scheduled in a sequence or calculated therefrom in a predetermined or even random routine. By way of example, the target heart rate may be entered as 145 bpm for 10 minutes, 25 percent lower (109 bpm) for 5 minutes and back to 145 bpm for 15 minutes.

These settings may be manually entered, entered by a key-card or other identifying device, or recalled from the internal memory 74. For example, a user may press a key to recall from the memory 74 his or her personal previously-entered settings. To this end, the apparatus 10 ordinarily includes a control console 94 which provides user data input devices 96 such as switches, keypads and the like connected to the input circuitry 76 of the controller 30, along with a visual display 98 connected to the output circuitry 76 of the controller 30.

Alternatively, certain of the parameters may be determined by the controller 30 based upon other information available thereto. For example, the controller 30 may determine the maximum or target heart rate based upon the age, weight and/or sex of the user. Moreover, rather than being directly input by the user, the maximum resistance levels of the resistance mechanisms 12, 14 may be based upon the resistance levels that are present when the measured heart rate of the user achieves the target heart rate, such as when concluding a warm-up mode as described below.

Once the necessary settings are entered, the apparatus preferably enters a warm-up mode at step 120 during which the user ordinarily increases his heart rate up to the target rate by manually increasing, through commands entered at the user input device 96, the resistance levels of the first and second resistance mechanisms 12, 14 up to the previously entered maximum limits.

Once the actual (average) heart rate equals or exceeds the entered target heart rate (step 122), the controller 30 begins executing software instructions in the target heart rate control mode of operation, referred to herein as the target mode. Note that as shown in FIG. 5A, throughout the warm-up mode the actual (average) heart rate is continually being updated, although as previously described, this preferably occurs as the pulses are detected and not at any specific time, and thus is shown as broken line step 124.

In accordance with the invention, as shown in FIGS. 5B–5C, once the target heart rate is reached, the actual (average) heart rate is maintained at the target heart rate for the scheduled time duration by adjusting the resistance level of the first resistance mechanism 12 with respect to the resistance level of the second resistance mechanism 14. However, for safety purposes the actual (average) heart rate is first compared at step 130 to determine if the actual rate exceeds the target heart rate by 20 bpm. If so, a dangerous condition is assumed, and at step 131 the controller activates an alarm 100 in console 94 and begins to shut down the treadmill in a predetermined shut down pattern, generally by rapidly reducing the grade and decelerating the speed in a manner that is gradual enough so that the user does not fall forward but that is still quick enough to significantly reduce the heart rate. Of course, rather than base the danger rate on the target rate plus 20 bpm, an actual upper limit may be utilized, although it first would need to be entered.

If the danger level has not been reached, the executing program moves to step 132 to determine if the actual rate exceeds the scheduled target heart rate by 14 bpm. If so, in the exemplified embodiment the workload (grade and/or speed resistance) is immediately reduced by twenty percent at step 133 in an attempt to quickly reduce the actual (average) heart rate before reaching a potentially dangerous level. This has been found to rapidly reduce the heart rate.

If the actual rate is below this warning level, at step 134 the program checks to determine if the time spent exercising in the target mode (i.e., the actual time not including the warm-up time) has exceeded the previously loaded total time duration. If so, the program preferably enters a reduced-workload cool down mode, described in more detail below.

If the exercise time has not exceeded the total time, the program effectively executes a delay at step 136, either by actually delaying or by skipping over any adjustment to the speed and grade until at least some minimum time has elapsed. In a preferred program, no actual delay is performed but an effective delay occurs by not performing any adjustment to the resistance mechanisms 12, 14 until at least eight seconds have elapsed since the previous adjustment. This prevents occasional bad heart rate detections or minor fluctuations from causing frequent adjustments to the machine that are only temporary and may in fact be incorrect.

Once enough time has elapsed, an adjustment may be forthcoming. At this time, at step 140 the program determines whether to increase or decrease the workload, or if an adjustment is even necessary, since the actual (average) rate may still be within plus-or-minus three bpm of the scheduled target heart rate wherein no adjustment is to be made.

However, in the exemplified embodiment the comparison of the scheduled target heart rate with the actual (average) rate is not entirely straightforward at this point, instead factoring in the acceleration, if any, of the most recently obtained (current) actual average heart rate from the previous heart rate. Although factoring in the heart rate acceleration is not necessary to the invention, it provides a way to adjust the workload in anticipation of the target heart rate being reached, preventing overshooting that is not predictable, and may at times be dangerous.

To accomplish the comparison, the difference in the previous (average) heart rate from the current (average) heart rate (acceleration factor) is combined with the difference of the current (average) heart rate from the scheduled target heart rate to determine the adjustment direction, if any. These differences can be weighted to obtain a desirable result in actual applications. Thus, it has been found that the following equation obtains a satisfactory result:

Adjustment direction=(Target heart rate−current heart rate)/3(Current heart rate−previous heart rate)/4.

Applying this equation as represented in the state machine diagram of FIG. 5B, if the adjustment direction is less than or equal to −1, the workload will be reduced, if greater than or equal to +1 the workload will be increased, and if between −1 and +1 the workload will remain the same. Preferably, so that the machine does not continually oscillate between two settings, this equation allows the actual (average) rate to vary between plus or minus three bpm of the entered target heart rate, although other reasonable ranges are equally feasible.

In one possibility, as represented in step 142 and in the state machine diagram of FIG. 5B, if no action is necessary the program loops back without making an adjustment. Note that even if no action is taken, the average heart rate continues to be calculated and/or updated whenever ready, as described above, at step 143.

If the comparison (step 144) results in a requested increase to the workload, i.e., the actual (average) heart rate is slower than the scheduled rate, (taking into consideration any acceleration factor, if desired), the level of resistance of the first resistance mechanism 12 is compared at step 146 to determine if it is already at its predetermined upper resistance level. As represented at step 148 and in the state machine diagram of FIG. 5C, the resistance level of the first resistance mechanism 12 is increased if not at this maximum level.

Thus, by way of example, if the first resistance mechanism 12 adjusts the speed of the treadmill 10, and the maximum speed entered for that particular user is 6.0 miles per hour, the controller 30 will supply a signal to the motor 16 to increase the speed and thereby the heart rate, regardless of the grade of the treadmill 10, if the speed of the treadmill 10 is below 6.0 miles per hour. If the next time through the loop the actual heart rate is again below the target level, this increasing of the speed will continue in one-tenth mile per hour increments up to the 6.0 mile per hour predetermined maximum. Thus, the speed will keep increasing up to the maximum entered speed, if necessary to increase the actual heart rate to the target level.

In keeping with the invention, if the actual heart rate is slower than the scheduled target heart rate and the first resistance mechanism 12 is already at the predetermined upper resistance level, as shown in step 50 and in the state machine diagram of FIG. 5C, the resistance level of the second resistance mechanism 14 is increased. Thus, in the above example, only when the 6.0 mile per hour predetermined maximum speed is reached will the grade be increased in an effort to further increase the heart rate to the target heart rate.

In the exemplified embodiment, if the second resistance mechanism 14 adjusts the grade of a treadmill 10, and the maximum grade is set to 4.0 percent, the controller 30 will supply a signal (step 152) to the incline motor 36 to increase the grade (and thereby increase the heart rate) when the maximum speed of the treadmill has been reached. Of course, the grade will not be increased if already at its maximum as indicated by step 150. This increasing of the grade will continue, in one-half percent increments each time through the loop, up to the 4.0 percent predetermined maximum, if necessary, to increase the actual (average) heart rate to the target level.

Figure 4D:
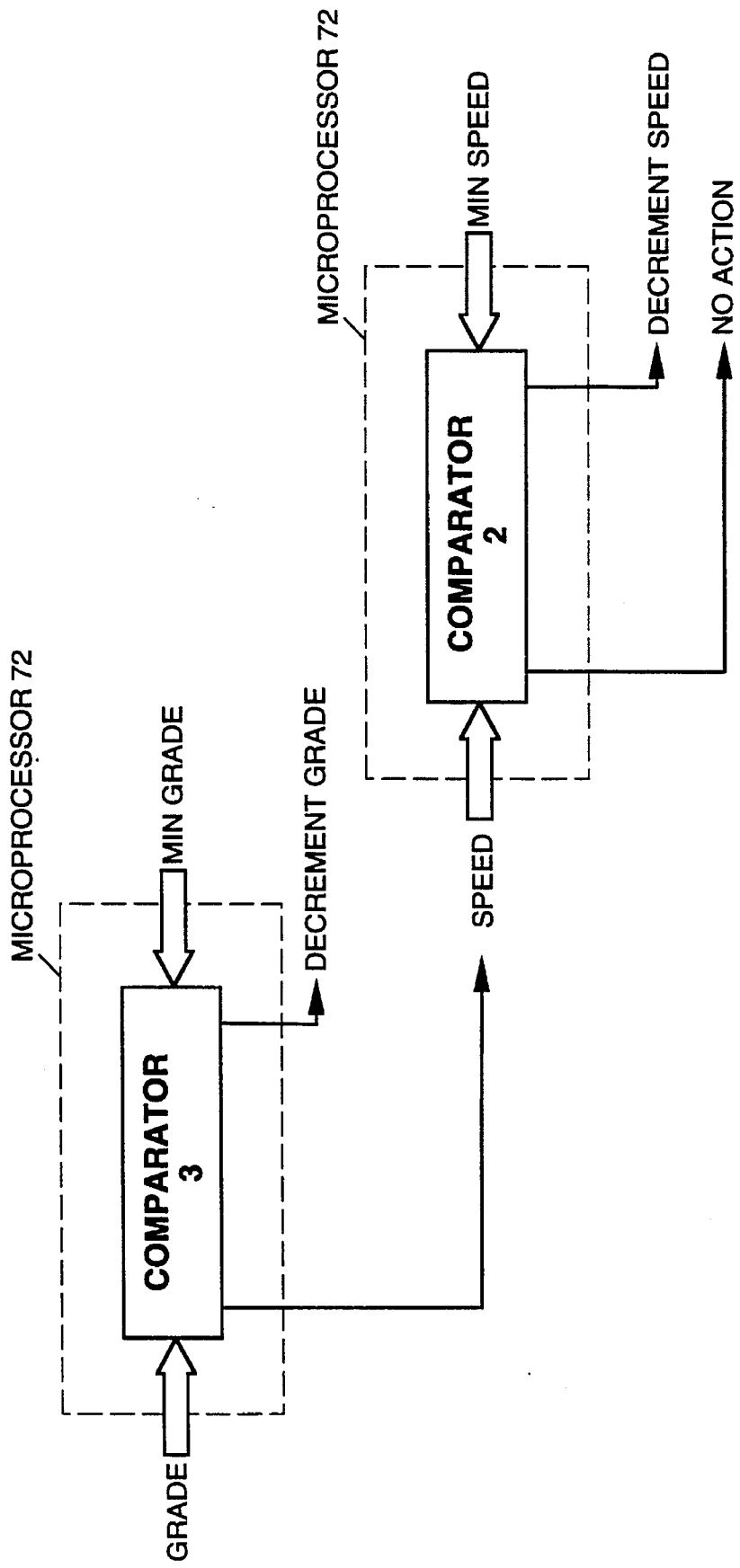

In the situation where the heart rate must be decreased, the workload is ordinarily removed in the reverse order. Thus, if the heart rate is faster than the scheduled rate and the second resistance mechanism 14 is not at a predetermined lower resistance level (step 154 and the state machine diagram of FIG. 4D), the resistance level of the second resistance mechanism is decreased at step 156. However, if the second resistance mechanism 14 is already at the predetermined lower resistance level, the resistance level of the first resistance mechanism 12 is decreased at step 160, provided it is not already at a minimum as determined at step 158.

Thus, in keeping with the example, to lower the actual heart rate, grade is first reduced to predetermined minimum level, ordinarily 0.0 percent, before any speed reduction occurs.

Of course, it can be readily appreciated that it is equivalent to alternatively consider the grade of the machine as the first resistance mechanism so that the grade is first increased to its maximum before the speed (second resistance mechanism) is adjusted. However, the manner described in detail herein has been found to favorably maintain the target heart rate. Moreover, as described previously, when reducing heart rate, the workload is preferably removed in the reverse order that it was added, Although not necessary to the invention, since some speed is always necessary, this pattern enables the apparatus to function in a repeatable manner.

It should be noted that with the present invention, not only may a number of target heart rates be sequenced together, but a number of corresponding maximum and minimum grades and speeds may be sequenced in time. By way of example, a user wishing to improve both speed and grade might first find it beneficial to have a very low maximum grade for a certain time duration, thus ensuring some training at a higher speed, and then having a low maximum speed for a certain duration thus ensuring some training at the higher grade. The ability of the apparatus to operate in these sequenced modes is even more apparent with an apparatus that exercises different muscle groups simultaneously, such as a combination bicycle/rowing machine, where a user might wish to maintain a certain heart rate yet exercise different muscles at different exertion levels that vary throughout an exercise routine.

In summary, the resistance mechanisms 12, 14 are incrementally varied as described above and the actual heart rate is ordinarily maintained at or near the target level for the time duration entered.

Figure 8:
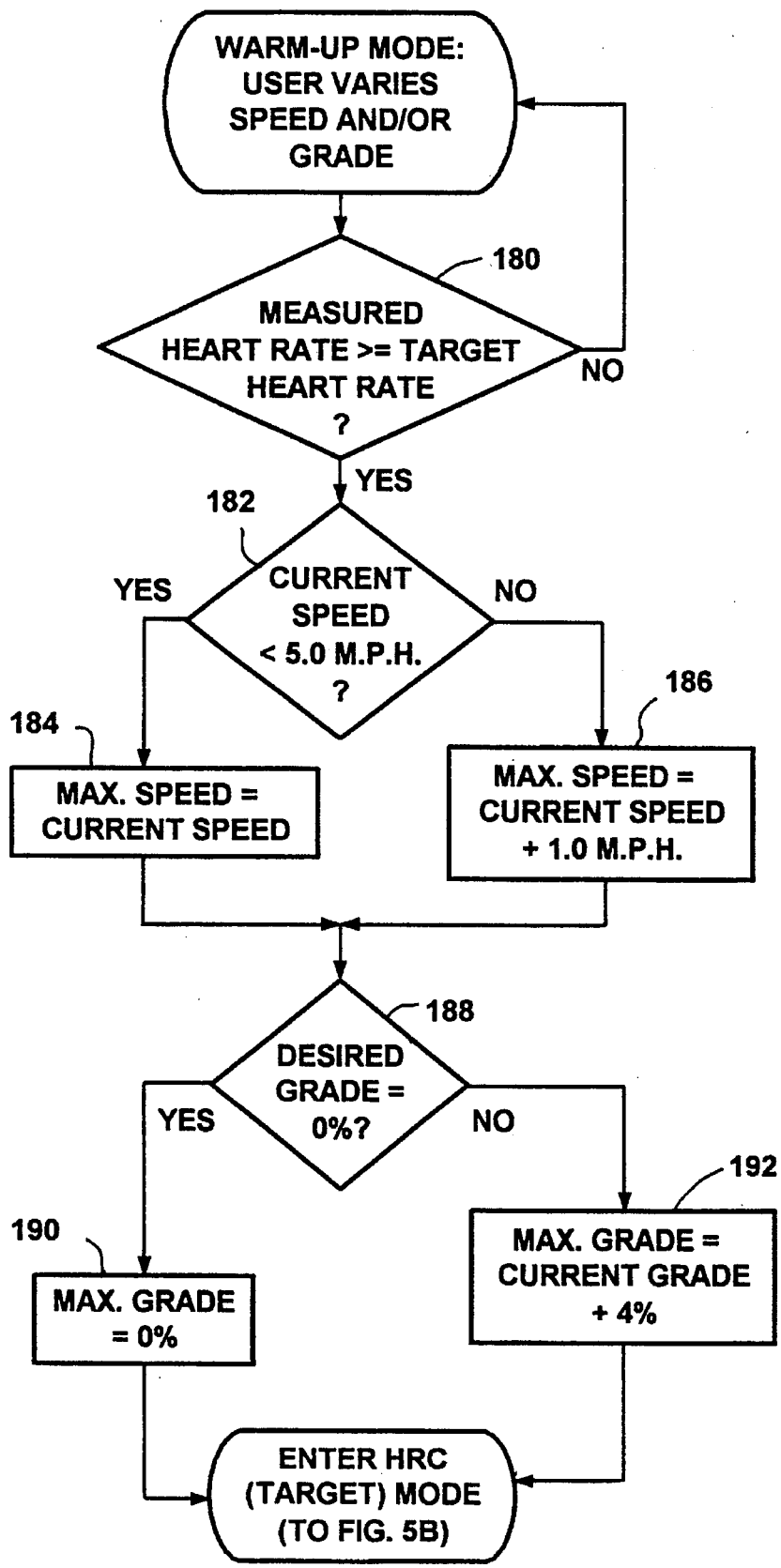
FIG. 8 is a flow diagram of the general controller software steps for determining the maximum speed and grade of a treadmill in one alternate embodiment according to the invention.

In one embodiment of the invention, as represented by the flow diagram of FIG. 8, the maximum resistance levels are determined by the resistance settings that the user is currently exercising at when the target heart rate is first achieved, i.e., at the conclusion of the warm-up mode. As shown in FIG. 8, at step 180 when the measured heart rate equals or exceeds the target heart rate, the warm-up mode is completed in the treadmill device. Before entering the heart rate control mode of the treadmill, however, the maximum speed and grade are determined by the controller 30 rather than being directly input by the user. To this end, the controller 30 determines the maximum speed and grade of the treadmill based upon the current speed and grade at the moment that the user reaches the target heart rate.

Thus, the current speed is evaluated at step 182 as soon as the target heart rate has been achieved. If the speed is less than five miles per hour at this time, the controller will set the maximum speed for that user to the current speed at step 184. Conversely, if the current speed is greater than five miles per hour at step 182, then at step 186 the controller sets the maximum speed for that user at the current measured speed plus one mile per hour. For example, a first user reaching his target heart rate at 3.5 miles per hour will be assigned a maximum speed of 3.5 miles per hour, while a second user reaching her target heart rate at 6.5 miles per hour will be assigned a maximum speed of 7.5 miles per hour.

If the user indicates that no grade is desired, such as by entering the target heart rate control mode with zero grade, no grade will be used. A user can accomplish this by simply not incrementing grade during the manually-controlled warm-up mode. The zero grade condition is checked at step 188 of FIG. 8, and, in the situation where the heart rate control mode was entered with zero grade, at step 190 the maximum grade is set to zero. Conversely, if the heart rate control mode was entered with a non-zero grade, at step 192 the maximum grade is set to four percent above the grade at which the heart rate control mode was entered. At this time, the heart rate control mode is entered and the resistance levels are adjusted up to these maximums in order to control the heart rate of the user as previously described.

The above target heart rate-based maximum values, including the five mile per hour cutoff before adding one mile per hour to the maximum speed, and either the zero grade or current grade plus four percent values, were selected so as to differentiate between walking and running workouts. By way of example of walking workouts, a user entering the heart rate control mode at 3.5 miles per hour and 4% grade will have maximums of 3.5 miles per hour and 8% grade, while a user entering the heart rate control mode at 4.2 miles per hour and 6% grade will have maximums of 4.2 miles per hour and 10% grade. By way of example of running workouts, a user entering the heart rate control mode at 6 miles per hour and 0% grade will have maximums of 7 miles per hour and 0% grade, while a user entering the heart rate control mode at 5 miles per hour and 2% grade will have maximums of 6 miles per hour and 6% grade.

In general, the controller 30 assumes that a walker will prefer to utilize grade and have the grade automatically varied to control the heart rate, while a runner will prefer to not use grade at all, allowing only speed variations to control the heart rate. However, while these assumptions generally provide the desired different types of workouts, it can be appreciated that values other than those exemplified herein may be substituted without departing from the spirit and scope of the present invention.

Although not necessary to the invention, at the end of the exercise routine, a cool-down mode is entered for an indefinite period of time wherein the grade is reduced to 0.0 percent and the speed is reduced by 40 percent to gradually lower the heart rate. During the cool-down mode, the user regains manual control of the speed and grade via the user input device 96.

Figure 6:
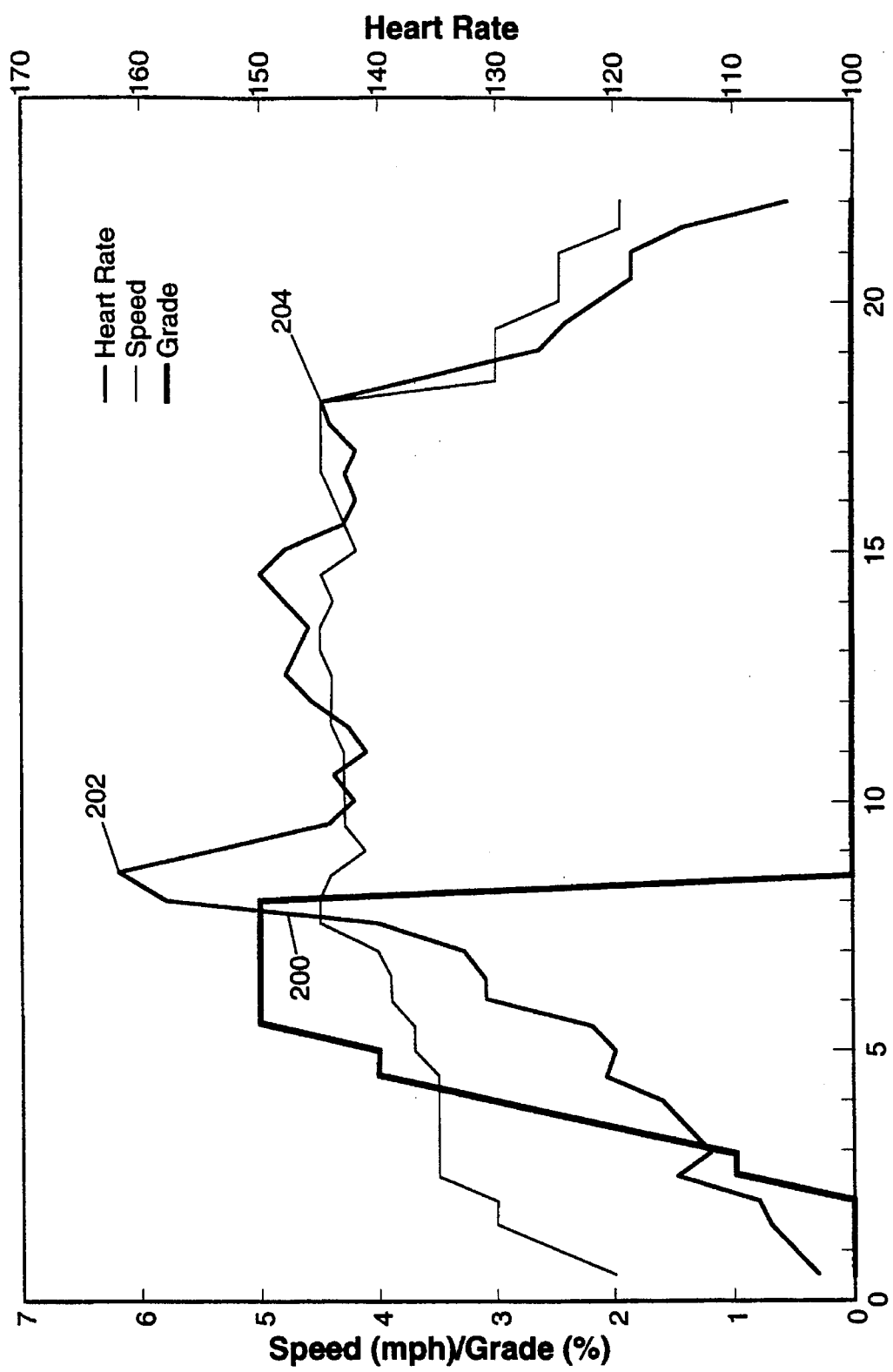
FIG. 6 is a graphical representation illustrating the heart rate of a first representative user relative to the settings of the resistance mechanisms of a treadmill.

By way of example, two representative graphs are included illustrating the actual heart rate with respect to the speed and grade of a treadmill over a period of time. In FIG. 6, a target heart rate of 145 bpm was entered, along with a maximum speed of 4.5 miles per hour and a maximum grade of 5.0 percent. The apparatus attempted to maintain the heart rate at the target (145 bpm) level for an entered total time duration of 10 minutes.

As shown in FIG. 6, a warm-up period occurred for approximately 7.5 minutes before the target level was reached, as indicated by point 200. As can be seen, during the warm-up mode the grade was manually increased to a maximum of 5.0 percent, while the speed was gradually increased to its maximum of 4.5 miles per hour.

Once the target mode was entered, which occurred automatically upon achieving the target heart rate, the twenty percent warning reduction occurred at point 202 as the actual heart rate (approximately 162 bpm) was more than 14 bpm above the target rate of 145 bpm. Accordingly, the grade was quickly reduced to 0.0 percent. From that point on, the speed was lowered as the heart rate increased or raised as the heart rate decreased as shown during the period between approximately 8.5 minutes and 17.5 minutes.

At point 204, or 17.5 minutes, the total time entered was exceeded and thus the executing routine entered the previously described cool-down mode. As can be seen, the speed was quickly reduced and the heart rate decreased accordingly.

Figure 7:
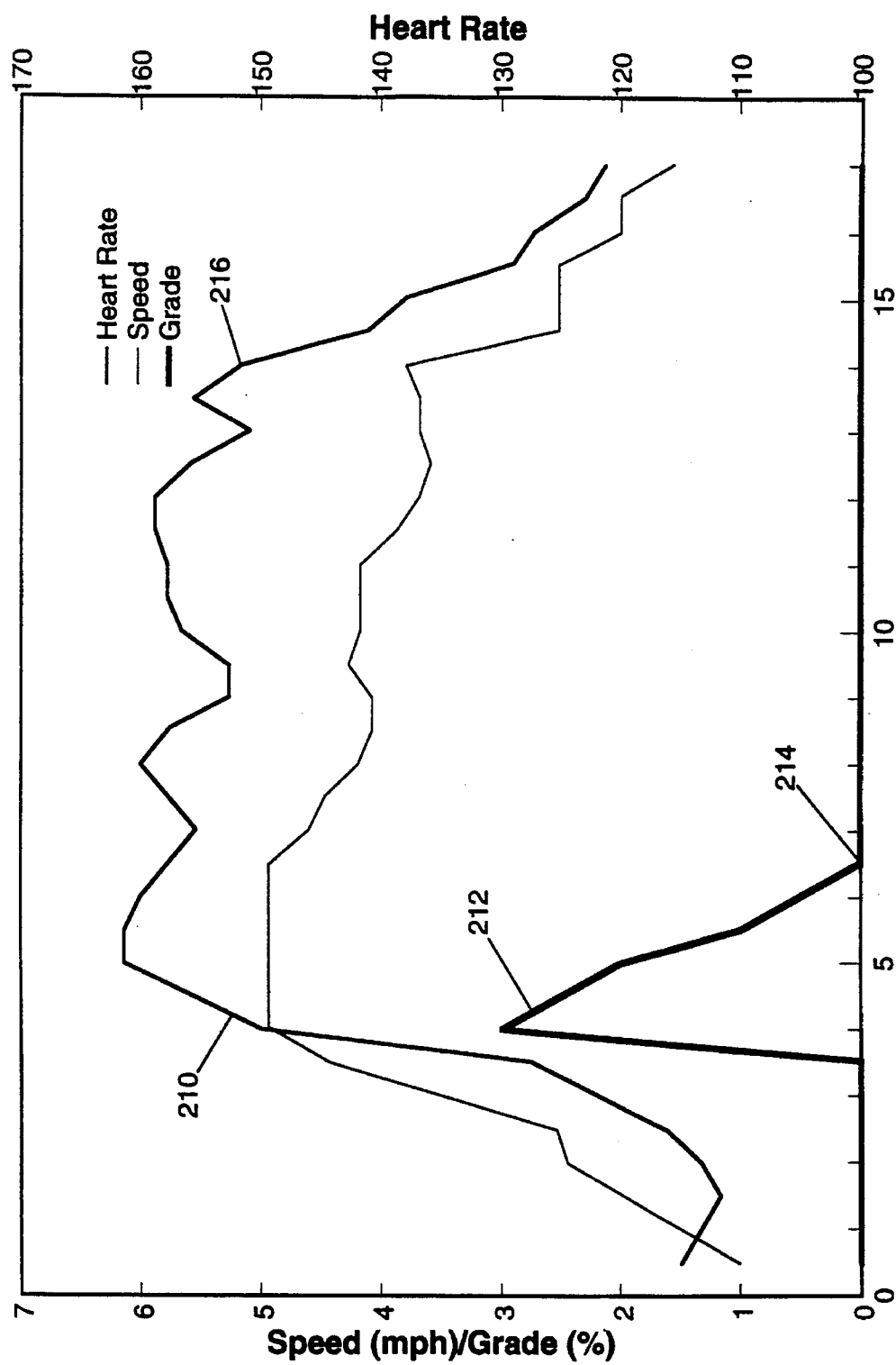
FIG. 7 is a graphical representation illustrating the heart rate of a second representative user relative to the settings of the resistance mechanisms of a treadmill.

In FIG. 7, a target heart rate of 155 bpm was entered, along with a maximum speed of 5.0 miles per hour and a maximum grade of 5.0 percent. The apparatus attempted to maintain the heart rate at the target (145 bpm) level for a total time duration of 10.5 minutes.

As shown in FIG. 7, a warm-up period occurred for approximately 4 minutes before the target level was reached, as indicated by point 210. As can be seen, during the warm-up mode the grade was manually increased to approximately 3.0 percent, while the speed was increased to its maximum of 5.0 miles per hour.

Once the target mode was entered, which occurred automatically upon achieving the target heart rate, in accordance with one aspect of the invention the grade was decreased by the controller 30 while the speed remained constant. Only when the grade was reduced to 0.0 percent, as indicated by point 114, was the speed varied (reduced). From that point on, only the speed was adjusted to maintain the heart rate at the target level, until at point 216 the cool-down mode was entered.

Finally, it can be appreciated that other modes of operation including conventional modes of operation and variations of the target mode may be implemented with the apparatus 10. Thus, for example, one alternative operating mode that has been found to be beneficial, described as an interval heart rate control mode, or interval mode, is based on the same general principles of the target mode, but further requires periods of rest times and work times that are ordinarily entered by the user or recalled from memory for that specific user.

In this interval mode, after a warm-up period to reach the target heart rate, the user automatically enters the first work time period wherein the system maintains the user at the target rate in the manner described above for the target mode. However, after the length of time entered for this work period expires, the user enters a rest period wherein the workload is reduced fifty percent, and the heart rate lowered, first by reducing grade, and then speed, if necessary. The system records the grade and speed that the user was previously at before any reduction occurred, and then returns the user to those levels at the end of the rest time. The system alternates between the work setting and the rest setting, with an overall tendency to reduce the amount of speed and grade in general throughout the interval mode, as the user tires from the workout thereby influencing the effects of the resistance on the heart rate.

It can be readily appreciated that other modes are also feasible since control of the resistance mechanisms can be varied over the time of the exercise in any number of ways and sequences. In addition, manual adjustment of the target heart rate (resulting in resistance adjustments) may be allowed at any time during operation, although for safety reasons this is ordinarily limited to plus or minus 10 bpm in the target mode of operation, and plus or minus 5 bpm in the interval mode of operation.

As can be seen from the foregoing description, there is provided a method and apparatus for dynamically controlling the resistance of a first resistance mechanism with respect to the resistance of at least one other resistance mechanism of a fitness apparatus in dependence on the heart rate of the user thereof. The fitness apparatus optimizes the benefit obtained from exercise thereon, and, since an individual user may input operational data, the apparatus and method is capable of benefitting virtually any user regardless of their level of physical conditioning. The fitness apparatus may further incorporate conventional features and alternative modes of operation, and ordinarily is combined with electronic heart rate supervision to ensure the safety of the user.

All of the references cited herein are hereby incorporated in their entireties by reference.

What is claimed is:

1. A method of setting maximum resistance levels in a fitness apparatus comprising the steps of, providing a fitness apparatus including first and second resistance mechanisms, a heart rate sensor, a first resistance sensor, a second resistance sensor, comparison circuitry, and a processor coupled to the comparison circuitry, the heart rate sensor, and the first and second resistance sensors; and setting maximum resistance levels of the first and second resistance mechanisms in accordance with a predetermined heart rate by (a) sensing the heart rate of the user while sensing resistance levels of the first and second resistance mechanisms; (b) comparing the sensed heart rate with the predetermined target rate; and (c) determining maximum resistance levels for the first and second resistance mechanisms based upon the resistance levels when the sensed heart rate equals or exceeds the predetermined target heart rate.

2. The method of claim 1 wherein the first resistance mechanism is a treadmill belt speed, and the step of determining maximum resistance level for the first resistance mechanism includes the step of measuring the treadmill belt speed when the sensed heart rate equals or exceeds the predetermined target heart rate.

3. The method of claim 2 wherein the maximum resistance level for the first resistance mechanism is set to the measured belt speed if the measured belt speed is five miles per hour or less, and is set to the measured belt speed plus one mile per hour if the measured belt speed is greater than five miles per hour.

4. The method of claim 1 wherein the first resistance mechanism is a treadmill grade, and the step of determining maximum resistance level for the second resistance mechanism includes the step of measuring the grade when the sensed heart rate equals or exceeds the predetermined target heart rate.

5. The method of claim 4 wherein the maximum resistance level for the second resistance mechanism is set to the measured grade plus four percent.

6. The method of claim 4 wherein the maximum resistance level for the second resistance is zero grade if the measured grade is zero when the sensed heart rate equals or exceeds the predetermined target heart rate.

7. In a treadmill having a variable belt speed and a variable grade, an apparatus for setting a maximum speed and a maximum grade, comprising, means for receiving a predetermined target heart rate, a heart rate sensor for sensing the heart rate of the user and providing a sensed heart rate value corresponding thereto, a speed sensor for sensing the belt speed and providing a current speed value corresponding thereto, a grade sensor for sensing the grade and providing a current grade value corresponding thereto, comparison circuitry for comparing the sensed heart rate with the predetermined target rate and for providing a signal when the sensed heart rate equals or exceeds the predetermined target heart rate, and a processor, the processor connected to the comparison circuitry to set a maximum speed based on the current speed value and a maximum grade based on the current grade value upon receipt of the signal.

8. The apparatus of claim 7 wherein the processor sets the maximum speed to the current sensed speed if the sensed speed is five miles per hour or less.

9. The apparatus of claim 7 wherein the processor sets the maximum speed to the current sensed speed plus one mile per hour if the sensed speed is greater than five miles per hour.

10. The apparatus of claim 7 wherein the processor sets the maximum grade to the current sensed grade.

11. The apparatus of claim 7 wherein the processor sets the maximum grade to the current sensed grade plus four percent.

* * * * *